United States Patent [19]
Willingham et al.

[11] Patent Number: 6,008,244
[45] Date of Patent: Dec. 28, 1999

[54] HALOPROPARGYL COMPOUNDS AS MARINE ANTIFOULING AGENTS

[75] Inventors: Gary Lewis Willingham, Glenside, Pa.; Samuel Eugene Sherba, Willingboro, N.J.; Barry Clifford Lange, Lansdale, Pa.

[73] Assignee: Rohm and Haas Company, Phila., Pa.

[21] Appl. No.: 08/948,182

[22] Filed: Oct. 9, 1997

[51] Int. Cl.⁶ .......................... A01N 43/00; A01N 43/36; A01N 43/40; A01N 43/46
[52] U.S. Cl. .......................... 514/428; 504/154; 504/155; 504/156; 504/158; 504/160; 514/211; 514/212; 514/227.5; 514/238.8; 514/315; 514/365; 514/372; 514/408
[58] Field of Search ...................................... 504/155, 154, 504/156, 158, 160; 514/428, 315, 238.8, 211, 212, 227.5, 365, 372, 408

[56] References Cited

U.S. PATENT DOCUMENTS 4,521,412 6/1985 Schmitt et al. .......................... 514/244

*Primary Examiner*—Allen J. Robinson
*Attorney, Agent, or Firm*—Thomas J. Howell; S. Matthew Cairns

[57] ABSTRACT

Disclosed is a method of inhibiting the growth of marine organisms on a marine structure, by applying onto or into the marine structure a halopropargyl quaternary ammonium compound, halopropargyl benzoxazolone compound, or halopropargylhydantoin compound. These compounds may be directly incorporated into the marine structure during manufacture, directly applied to the structure, or applied to the structure by means of a coating.

9 Claims, No Drawings

HALOPROPARGYL COMPOUNDS AS MARINE ANTIFOULING AGENTS

BACKGROUND OF THE INVENTION

This invention relates generally to a method of inhibiting the growth of organisms on a marine structure. In particular, this invention relates to the use of certain halopropargyl compounds as marine antifouling agents.

Marine antifouling agents are used commercially to prevent growth of organisms on marine structures. Tributyltin oxide and other organotins have been the major marine antifouling agents in use for many years. There is currently much concern over the effects of tin on marine environments. For example, high levels of tin in harbor waters have been linked to shell deformation in some bivalve species, such as oysters.

Some organic compounds have been suggested as marine antifoulants. For example, U.S. Pat. No. 5,071,479 (Gruening) discloses the use of 3-iodopropargyl N-butyl carbamate as marine antifouling agents. These types of compounds have not achieved commercial prominence because they do not meet the same performance requirements as tin based antifouling agents.

A number of cyclic N-halopropargyl substituted compounds and N-halopropargyl substituted quaternary ammonium compounds are known in the art as microbicides. See, for example, U.S. Pat. No. 5,411,933 (Hsu), which discloses bromopropargyl quaternary ammonium compounds as microbicides. These compounds are not disclosed as marine antifouling agents.

The effectiveness of microbicidal materials useful in combatting fungi, bacteria and the like in non-aqueous media, and microbicides effective in combatting fungi, slime, and algae in fresh water systems, cannot be used to predict the effectiveness of these compounds as marine antifouling agents in sea water and brackish water capable of supporting marine life such as barnacles, slime, hydroids, grassy brown felt algae, and the like.

The problem addressed by this invention is to provide marine antifouling agents having increased performance and little or no harmful effects to marine environments.

STATEMENT OF THE INVENTION

The present invention provides a method of inhibiting the growth of marine organisms on a marine structure, comprising applying onto or into the marine structure an effective amount of a marine antifouling agent selected from the group consisting of compounds of formulae:

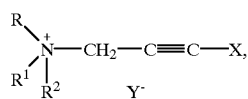

(I)

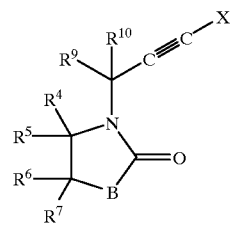

(II)

wherein:
R=($C_1$–$C_{16}$) alkyl or ($C_1$–$C_5$) alkyl substituted with C(C=O)$R^3$;
$R_1$ and $R_2$ are independently selected from ($C_1$–$C_3$) alkyl, or $R^1$ and $R^2$ are the same and are ($C_6$–$C_2$) alkyl; or $R_1$ and $R_2$ together to form a 5- to 7-membered ring selected from the group consisting of pyrrolidinium, piperidinium, morpholinium, dimethylmorpholinium, hexamethyleneiminium, thiomorpholinium, and thiazolidinium, optionally substituted with one or more ($C_1$–$C_3$) alkyl groups;
$R^3$=($C_6$–$C_{12}$) alkoxy;
B=O or $NR^8$, provided that when B=$NR^8$, $R^4$ and $R^5$=O or $R^6$ and $R^7$=O but not both, and further provided that when B=O, $R^4$ and $R^6$ taken together form a double bond and $R^5$ and $R^7$ taken together form a phenyl ring optionally substituted with halogen, nitro, ($C_1$–$C_4$) alkyl, ($C_1$–$C_4$) alkoxy, cyano, C(O)O($C_1$–$C_4$) alkyl, C(O)OPhenyl, and ($C_1$–$C_4$) haloalkyl;
$R^8$=($C_1$–$C_{12}$) alkyl; benzyl; phenyl optionally substituted with halogen, nitro, cyano, ($C_1$–$C_3$) haloalkyl; ($C_1$–$C_3$) alkoxy; allyl; ($C_3$–$C_6$) alkynyl optionally substituted with halogen; and H;
$R^4$, $R^3$, $R^6$, and $R^7$ are independently selected from H; ($C_1$–$C_3$) alkyl; phenyl optionally substituted with halogen, nitro, ($C_1$–$C_3$) alkoxy, and ($C_1$–$C_3$) haloalkyl; or $R^4$ and $R^5$ or $R^6$ and $R^7$ together form a ($C_3$–$C_7$) saturated or a ($C_5$–$C_7$) unsaturated spirocycle;
$R^9$ and $R^{10}$ are independently selected from H or ($C_1$–$C_3$) alkyl;
X=halogen; and
Y=an anion.

DETAILED DESCRIPTION OF THE INVENTION

As used herein, marine antifouling agents include algaecides and molluscicides. Marine antifoulant activity is intended to include both the elimination of and inhibition or prevention of growth of marine organisms. Marine organisms controlled by the marine antifouling agents suitable for use in this invention include both hard and soft fouling organisms. Generally speaking, the term "soft fouling organisms" refers to plants and invertebrates, such as algae, kelp, soft corals, tunicates, hydroids, sponges, and anemones and the term "hard fouling organisms" refers to invertebrates having some type of hard outer shell, such as barnacles, tubeworms and molluscs.

As used in this specification, "spirocycle" means two ring systems having one carbon atom in common; "alkyl" means straight chain, branched, cyclic, or any combination thereof; and "halogen" means fluorine, chlorine, bromine, or iodine.

As used in this specification, all amounts are percent by weight ("% wt") unless otherwise noted. All % wt ranges are inclusive. The following abbreviations are used: mL=milliliter, μL=microliter, g=grams, μg/mL=micrograms per milliliter, ppm=parts per million, mm=millimeter, nm=nanoeter, μm=micrometer, DMSO=dimethyl sulphoxide, DMF=dimethyl formamide, ASTM=American Society for Testing and Materials, and Abs=absorbance.

The compounds useful as marine antifouling agents in the present invention are those of formulae (I) or (II), above. Preferred compounds of formulae (I) and (II) are those wherein X is bromine or iodine. Preferred compounds of formula (I) are those wherein Y is selected from the group consisting of halogen, phosphate, acetate, benzoate, citrate, tartrate, alkylsulfonate, arylsulfonate, or alkylsulfate. Suitable alkylsulfonates include, but are not limited to, methanesulfonate and n-butanesulfonate. Suitable arylsulfonates include, but are not limited to, benzenesulfonate and 4-methylbenzenesulfonate.

Preferred compounds of the invention include the following:

| No. | Compound Name |
|---|---|
| 1 | 1-tetradecyl-1-(3-bromopropargyl)-pyrrolidinium 4-methylbenzenesulfonate |
| 2 | 1-tetradecyl-1-(3-bromopropargyl)-morpholinium benzenesulfonate |
| 3 | 1-tetradecyl-1-(3-bromopropargyl)-morpholinium 4-methyl-benzenesulfonate |
| 4 | 1-tetradecyl-1-(3-bromopropargyl)-morpholinium methanesulfonate |
| 5 | 1-tetradecyl-1-(3-bromopropargyl)-pyrrolidinium benzenesulfonate |
| 6 | 1-tetradecyl-1-(3-bromopropargyl)-piperidinium methanesulfonate |
| 7 | 1-tetradecyl-1-(3-bromopropargyl)-morpholinium n-butanesulfonate |
| 8 | 1-tetradecyl-1-(3-bromopropargyl)-pyrrolidinium n-butanesulfonate |
| 9 | 1-tetradecyl-1-(3-bromopropargyl)-morpholinium bromide |
| 10 | 1-tridecyl-1-(3-bromopropargyl)-morpholinium bromide |
| 11 | 1-hexadecyl-1-(3-bromopropargyl)-morpholinium bromide |
| 12 | 1-dodecyl-1-(3-bromopropargyl)-morpholinium 4-methylbenzenesulfonate |
| 13 | 1-hexadecyl-1-(3-bromopropargyl)-morpholinium methanesulfonate |
| 14 | 1-tetradecyl-1-(3-bromopropargyl)-2-methyl-piperidinium 4-methylbenzenesulfonate |
| 15 | 1-tetradecyl-1-(3-bromopropargyl)-2-methyl-piperidinium 4-methylbenzenesulfonate |
| 16 | 1-tetradecyl-1-(3-bromopropargyl)-2-methyl-piperidinium benzenesulfonate |
| 17 | 1-tetradecyl-1-(3-bromopropargyl)-piperidinium benzenesulfonate |
| 18 | trioctyl-(3-bromopropargyl)ammonium benzenesulfonate |
| 19 | dimethyloctyl(3-bromopropargyl)ammonium benzenesulfonate |
| 20 | trioctyl(3-bromopropargyl)ammonium 4-methylbenzenesulfonate |
| 21 | dimethyldodecylammonium 4-methylbenzenesulfonate |
| 22 | trihexyl(3-bromopropargyl)ammonium benzenesulfonate |
| 23 | trihexyl(3-bromopropargyl)ammonium 4-methylbenzenesulfonate |
| 24 | tridodecyl(3-bromopropargyl)ammonium 4-methylbenzenesulfonate |
| 25 | methyldioctyl(3-bromopropargyl)ammonium 4-methylbenzenesulfonate |
| 26 | methyldioctyl(3-bromopropargyl)ammonium benzenesulfonate |
| 27 | tri-iso-octyl(3-bromopropargyl)ammonium benzenesulfonate |
| 28 | tri-iso-decyl(3-bromopropargyl)ammonium benzenesulfonate |
| 29 | tri-n-nonyl(3-bromopropargyl)ammonium benzenesulfonate |
| 30 | tri-n-decyl(3-bromopropargyl)ammonium benzenesulfonate |
| 31 | 1-(2-hydroxyethyl)-1-(3-iodopropargyl)-pyrrolidinium 4-methyl-benzenesulfonate |
| 32 | 1-(12-hydroxydodecyl)-1-(3-iodopropargyl)-pyrrolidinium 4-methylbenzenesulfonate |
| 33 | 1-(8-hydroxyoctyl)-1-(3-iodopropargyl)-pyrrolidinium 4-methyl-benzenesulfonate |
| 34 | 1-(7-hydroxyheptyl)-1-(3-iodopropargyl)-pyrrolidinium 4-methyl-benzenesulfonate |
| 35 | 1-(9-hydroxynonyl)-1-(3-iodopropargyl)-pyrrolidinium 4-methyl-benzenesulfonate |
| 36 | 1-tetradecyl-1-(3-iodopropargyl)-pyrrolidinium 4-methyl-benzenesulfonate |
| 37 | 1-hexadecyl-1-(3-iodopropargyl)-pyrrolidinium 4-methyl-benzenesulfonate |
| 38 | 1-tridecyl-1-(3-iodopropargyl)-pyrrolidinium 4-methyl-benzenesulfonate |
| 39 | 1-butyl-1-(3-iodopropargyl)-pyrrolidinium 4-methyl-benzenesulfonate |
| 40 | 1-pentadecyl-1-(3-iodopropargyl)-pyrrolidinium 4-methyl-benzenesulfonate |
| 41 | 1-decyl-1-(3-iodopropargyl)-pyrrolidinium 4-methyl-benzenesulfonate |
| 42 | 1-octyl-1-(3-iodopropargyl)-pyrrolidinium 4-methyl-benzenesulfonate |
| 43 | 1-dodecyl-1-(3-iodopropargyl)-pyrrolidinium 4-methyl-benzenesulfonate |
| 44 | 1-hexyl-1-(3-iodopropargyl)-pyrrolidinium 4-methyl-benzenesulfonate |
| 45 | 1-undecyl-1-(3-iodopropargyl)-pyrrolidinium 4-methyl-benzenesulfonate |
| 46 | 1-octadecyl-1-(3-iodopropargyl)-pyrrolidinium 4-methyl-benzenesulfonate |
| 47 | 1-methyl-1-(3-iodopropargyl)-piperidinium 4-methyl-benzenesulfonate |
| 48 | 1-(2-hydroxyethyl)-1-(3-iodopropargyl)-piperidinium 4-methylbenzenesulfonate |
| 49 | 1-(11-hydroxyundecyl)-1-(3-iodopropargyl)-piperidinium 4-methylbenzenesulfonate |
| 50 | 1-(12-hydroxydodecyl)-1-(3-iodopropargyl)-piperidinium 4-methylbenzenesulfonate |
| 51 | 1-(9-hydroxynonly)-1-(3-iodopropargyl)-piperidinium 4-methylbenzenesulfonate |
| 52 | 1-(2-ethoxycarbonylethyl)-1-(3-iodopropargyl)-piperidinium 4-methylbenzenesulfonate |
| 53 | 1-(8-hydroxyoctyl)-1-(3-iodopropargyl)-piperidinium 4-methylbenzenesulfonate |
| 54 | 1-(7-hydroxyheptyl)-1-(3-iodopropargyl)-piperidinium 4-methylbenzenesulfonate |
| 55 | 1-(tetradecyl)-1-(3-iodopropargyl)-piperidinium 4-methylbenzenesulfonate |
| 56 | 1-(hexadecyl)-1-(3-iodopropargyl)-piperidinium 4-methylbenzenesulfonate |
| 57 | 1-(12-hydroxydodecyl)-1-(3-iodopropargyl)-tetramethyleneiminium 4-methylbenzenesulfonate |
| 58 | 4-tetradecyl-4-(3-iodopropargyl)-morpholinium 4-methyl-benzenesulfonate |
| 59 | 4-methyl-4-(3-iodopropargyl)-morpholinium 4-methyl-benzenesulfonate |
| 60 | 1-dodecyl-1-(3-iodopropargyl)-pyrrolidinium benzenesulfonate |
| 61 | 1-tridecyl-1-(3-iodopropargyl)-pyrrolidinium benzenesulfonate |
| 62 | 1-hexadecyl-1-(3-iodopropargyl)-pyrrolidinium benzenesulfonate |
| 63 | 1-pentadecyl-1-(3-iodopropargyl)-pyrrolidinium benzenesulfonate |
| 64 | 1-tetradecyl-1-(3-iodopropargyl)-pyrrolidinium benzenesulfonate |
| 65 | 1-hexadecyl-1-(3-iodopropargyl)-pyrrolidinium methanesulfonate |
| 66 | 1-tridecyl-1-(3-iodopropargyl)-pyrrolidinium methanesulfonate |
| 67 | 1-dodecyl-1-(3-iodopropargyl)-pyrrolidinium methanesulfonate |
| 68 | 1-pentadecyl-1-(3-iodopropargyl)-pyrrolidinium methanesulfonate |
| 69 | 1-tetradecyl-1-(3-iodopropargyl)-pyrrolidinium methanesulfonate |
| 70 | 1-hexadecyl-1-(3-iodopropargyl)-morpholinium methanesulfonate |
| 71 | 4-tetradecyl-4-(3-iodopropargyl)-morpholinium bemzenesulfonate |
| 72 | 4-tetradecyl-4-(3-iodopropargyl)-morpholinium methanesulfonate |
| 73 | 4-tetradecyl-4-(3-iodopropargyl)-2,6-dimethylmorpholinium 4-methylbenzenesulfonate |
| 74 | 1-hexadecyl-1-(3-iodopropargyl)-tetramethyleneiminium 4-methylbenzenesulfonate |
| 75 | 1-tetradecyl-1-(3-iodopropargyl)-tetramethyleneiminium 4-methylbenzenesulfonate |
| 76 | 4-hexadecyl-4-(3-iodopropargyl)-2,6-dimethylmorpholinium 4-methylbenzenesulfonate |
| 77 | 4-hexadecyl-4-(3-iodopropargyl)-2,6-dimethylmorpholinium benzenesulfonate |
| 78 | 4-hexadecyl-4-(3-iodopropargyl)-2,6-dimethylmorpholinium methanesulfonate |
| 79 | 4-hexadecyl-4-(3-iodopropargyl)-morpholinium 4-methyl-benzenesulfonate |
| 80 | 4-hexadecyl-4-(3-iodopropargyl)-morpholinium benzenesulfonate |
| 81 | 1-(tetradecyl)-1-(3-iodopropargyl)-2-methyl-piperidinium benzenesulfonate |
| 82 | 1-(tetradecyl)-1-(3-iodopropargyl)-4-methyl-piperidinium benzenesulfonate |
| 83 | 1-(tetradecyl)-1-(3-iodopropargyl)-1,2,3,6-tetrahydropyridinium |

| No. | Compound Name |
|---|---|
| | benzenesulfonate |
| 84 | 1-(tetradecyl)-1-(3-iodopropargyl)-2-methyl-piperidinium 4-methylbenzenesulfonate |
| 85 | 1-(tetradecyl)-1-(3-iodopropargyl)-2-methyl-piperidinium methanesulfonate |
| 86 | 1-(tetradecyl)-1-(3-iodopropargyl)-imidazolinium benzenesulfonate |
| 87 | 4-(tetradecyl)-4-(3-iodopropargyl)-thiomorpholinium benzenesulfonate |
| 88 | 3-(tetradecyl)-3-(3-iodopropargyl)-imidazolinium benzenesulfonate |
| 89 | 1-(tetradecyl)-1-(3-iodopropargyl)-piperidinium benzenesulfonate |
| 90 | 1-hexadecyl-1-(3-iodopropargyl)-piperidinium benzenesulfonate |
| 91 | 1-hexadecyl-1-(3-iodopropargyl)-piperidinium methanesulfonate |
| 92 | 1-(tetradecyl)-1-(3-iodopropargyl)-piperidinium methanesulfonate |
| 93 | 1-(dodecyloxycarbonyl)methyl-1-(3-iodopropargyl)-pyrrolidinium 4-methylbenzenesulfonate |
| 94 | 1-(dodecyloxycarbonyl)methyl-1-(3-iodopropargyl)-pyrrolidinium benzenesulfonate |
| 95 | 1-(decyloxycarbonyl)methyl-1-(3-iodopropargyl)-pyrrolidinium 4-methylbenzenesulfonate |
| 96 | 4-(decyloxycarbonyl)methyl-4-(3-iodopropargyl)-morpholinium 4-methylbenzenesulfonate |
| 97 | 4-(decyloxycarbonyl)methyl-4-(3-iodopropargyl)-morpholinium benzenesulfonate |
| 98 | 4-(dodecyloxycarbonyl)methyl-4-(3-iodopropargyl)-morpholinium 4-methylbenzenesulfonate |
| 99 | 1-(tetradecyl)-1-(3-iodopropargyl)-pyrrolidinium bromide |
| 100 | 1-(decyloxycarbonyl)methyl-1-(3-iodopropargyl)-pyrrolidinium benzenesulfonate |
| 101 | 4-(tetradecyl)-4-(3-iodopropargyl)-morpholinium bromide |
| 102 | 4-(tetradecyl)-4-(3-iodopropargyl)-morpholinium iodide |
| 103 | 4-benzyl-4-(3-iodopropargyl)-morpholinium 4-methylbenzenesulfonate |
| 104 | 4-benzyl-4-(3-iodopropargyl)-morpholinium methanesulfonate |
| 105 | 1-(dodecyloxycarbonyl)methyl-1-(3-iodopropargyl)-pyrrolidinium methanesulfonate |
| 106 | 4-(dodecyloxycarbonyl)methyl-4-(3-iodopropargyl)-morpholinium methanesulfonate |
| 107 | 1-n-butyl-1-(3-iodopropargyl)-pyrrolidinium bromide |
| 108 | 1-decyl-1-(3-iodopropargyl)-pyrrolidinium bromide |
| 109 | 1-dodecyl-1-(3-iodopropargyl)-pyrrolidinium bromide |
| 110 | 1-hexadecyl-1-(3-iodopropargyl)-pyrrolidinium bromide |
| 111 | 4-[5-(hexyloxycarbonyl)]pentyl-4-(3-iodopropargyl)-morpholinium 4-methylbenzenesulfonate |
| 112 | 1-[5-(hexyloxycarbonyl)]pentyl-4-(3-iodopropargyl)-pyrrolidinium 4-methylbenzenesulfonate |
| 113 | 4-[5-(hexyloxycarbonyl)]pentyl-4-(3-iodopropargyl)-morpholinium methanesulfonate |
| 114 | 1-[5-(hexyloxycarbonyl)]pentyl-1-(3-iodopropargyl)-morpholinium methanesulfonate |
| 115 | 1-(tetradecyl)-1-(3-iodopropargyl)-piperidinium n-butylsulfonate |
| 116 | 4-(tetradecyl)-4-(3-iodopropargyl)-morpholinium n-butylsulfonate |
| 117 | 1-(tetradecyl)-1-(3-iodopropargyl)-pyrrolidinium n-butylsulfonate |
| 118 | 4-pentadecyl-4-(3-iodopropargyl)-morpholinium methanesulfonate |
| 119 | 4-tridecyl-4-(3-iodopropargyl)-morpholinium methanesulfonate |
| 120 | 4-dodecyl-4-(3-iodopropargyl)-morpholinium methanesulfonate |
| 121 | 4-decyl-4-(3-iodopropargyl)-morpholinium methanesulfonate |
| 122 | 4-n-octyl-4-(3-iodopropargyl)-morpholinium methanesulfonate |
| 123 | 4-n-butyl-4-(3-iodopropargyl)-morpholinium methanesulfonate |
| 124 | 4-ethyl-4-(3-iodopropargyl)-morpholinium methanesulfonate |
| 125 | 4-[2-(decyloxycarbonyl)]ethyl-4-(3-iodopropargyl)-morpholinium methanesulfonate |
| 126 | 4-[2-(decyloxycarbonyl)]ethyl-4-(3-iodopropargyl)-morpholinium 4-methylbenzenesulfonate |
| 127 | 1-[2-(decyloxycarbonyl)]ethyl-1-(3-iodopropargyl)-pyrrolidinium 4-methylbenzenesulfonate |
| 128 | 1-[2-(decyloxycarbonyl)]ethyl-1-(3-iodopropargyl)-pyrrolidinium methanesulfonate |
| 129 | 4-n-butyl-4-(3-iodopropargyl)-morpholinium bromide |
| 130 | 4-hexadecyl-4-(3-iodopropargyl)-morpholinium bromide |
| 131 | 1-(3-iodopropargyl)-3-(3,5-dichlorophenyl)-5-methylhydantoin |
| 132 | 1-(3-iodopropargyl)-3-(3,5-dichlorophenyl)-5-methylhydantoin |
| 133 | 1-(3-iodopropargyl)-3-(4-chlorophenyl)-5-methylhydantoin |
| 134 | 1-(3-iodopropargyl)-3-(4-fluorophenyl)-5-methylhydantoin |
| 135 | 1-(3-iodopropargyl)-3-(3,5-dichlorophenyl)-5,5-spirocyclohexane-hydantoin |
| 136 | 1-(3-iodopropargyl)-3-(3,5-dichlorophenyl)-5,5-dimethylhydantoin |
| 137 | 1-(3-iodopropargyl)-3-(3,5-dichlorophenyl)hydantoin |
| 138 | 1-(3-iodopropargyl)-3-benzyl-5,5-dimethylhydantoin |
| 139 | 1-(3-iodopropargyl)-3-n-butyl-5,5-dimethylhydantoin |
| 140 | 1-(3-iodopropargyl)-3-n-octyl-5,5-dimethylhydantoin |
| 141 | 1,3-bis-(3-iodopropargyl)-5,5-dimethylhydantoin |
| 142 | 3-(3-iodopropargyl)-5,5-dimethylhydantoin |
| 143 | 1-(1,1-dimethyl-3-iodopropargyl)-3-(3,5-dichlorophenyl)-hydantoin |
| 144 | 3-(3-iodopropargyl)-1-benzyl-5,5-dimethylhydantoin |
| 145 | 3-(3-iodopropargyl)-hydantoin |
| 146 | 3-(3-iodopropargyl)-2-benzoxazolone |

The preparation of the compounds of the present invention are known in the literature. For example, bromopropargyl quaternary ammonium compounds can be prepared by the reaction of a tertiary amine with a bromopropargyl halide or sulfonate in a suitable solvent, such as acetone, methylene chloride, acetonitrile, water, and the like, at a temperature between 20 and 100° C. The synthesis of the bromopropargyl quaternary ammonium compounds can be found in U.S. Pat. No. 5,411,933 (Hsu), which is hereby incorporated by reference.

Iodopropargyl cyclic quaternary ammonium compounds can be prepared by reacting a cyclic amine with an iodopropargyl halide or sulfonate in a suitable solvent at a temperature between 0 and 100° C. Both the cyclic amines and the iodopropargyl halides or sulfonates are generally commercially available, for example, from Aldrich Chemical Company. The synthesis of the iodopropargyl cyclic quaternary ammonium compounds can be found in U.S. Pat. No. 5,266,567 (Hsu), which is hereby incorporated by reference.

Iodopropargyl hydantoin compounds can be prepared by propargylating hydantoins to yield N-propargylhydantoin compounds, which can be transformed into N-iodopropargylhydantoin compounds by use of a suitable iodinating agent, such as iodine, iodine-amino complex, or N-iodosuccinimide. The synthesis of iodopropargyl hydantoin compounds can be found in U.S. Pat. No. 5,346,913 (Hsu), which is hereby incorporated by reference.

Iodopropargyl benzoxazolone compounds can be prepared either by alkylating benzoxazolone compounds with iodopropargyl halide or by alkylating a benzoxazolone with a propargyl halide and subsequently iodinating with a suitable iodinating agent, such as iodine, iodine-amino complex, or N-iodosuccinimide. The synthesis of the iodopropargyl benzoxazolone compounds can be found in U.S. Pat. No. 5,102,898 (Hsu), which is hereby incorporated by reference.

The marine antifouling agents of the present invention can be used to inhibit the growth of marine organisms by application of an effective amount of one or more of the marine antifouling agents onto or into a marine structure. Depending upon the particular structure to be protected, the marine antifouling agents of the present invention can be directly incorporated into a structure, applied directly to the structure, or incorporated into a coating which is then applied to the structure.

Suitable structures include, but are not limited to: boats, ships, oil platforms, piers, pilings, docks, elastomeric rubbers, and fish nets. The marine antifouling agents of the present invention are typically directly incorporated into structures such as elastomeric rubber or fish net fibers during manufacture. Direct application of the compounds of the invention is typically made to structures such as fish nets or wood pilings. The compounds of the invention can also be incorporated into a marine coating, such as a marine paint or varnish.

In general, the amount of marine antifouling agent necessary to inhibit or prevent the growth of marine organisms is from 0.1 to 30% wt based on the weight of the structure to be protected or based on the weight of the coating to be applied. When the marine antifouling agents of the invention are directly incorporated into or directly applied onto a structure, the amount of the antifouling agent suitable to inhibit the growth of marine organisms is generally from 0.1 to 30% wt based on the weight of the structure to be protected. It is preferred to use an amount from 0.5 to 20% wt, and more preferably, from 1 to 15% wt. When incorporated into a coating, the amount of marine antifouling agent suitable to inhibit the growth of marine organisms is generally from 0.1 to 30% wt based on the weight of said coating. The amount of marine antifouling agent is preferably from 0.5 to 15% wt, and more preferably, from 1 to 10% wt.

If one of the marine antifouling agents of the invention is to be combined with a second marine antifouling agent, the ratio of the first marine antifouling agent to the second marine antifouling agent is from 99:1 to 1:99, preferably, from 75:25 to 25:75. The total of the combined marine antifouling agents necessary to inhibit or prevent the growth of marine organisms is from 0.1 to 30% wt based on the weight of the structure to be protected or the weight of the coating to be applied.

In general, the marine antifouling agents of the invention are incorporated in a carrier such as water; organic solvent, such as xylene, methyl isobutyl ketone, and methyl isoamyl ketone; or mixtures thereof.

Direct applications of the marine antifouling agents of the invention may be by any conventional means, such as dipping, spraying, or coating. Fish nets, for example, may be also protected by dipping the fish nets into a composition comprising one or more of the compounds of the invention and a carrier or by spraying the fish nets with said composition.

Structures such as wood pilings and fish nets may be protected by directly incorporating the marine antifouling agents into the structure. For example, a composition comprising one or more marine antifouling agents in a carrier may be applied to wood used for pilings by means of pressure treatment or vacuum impregnation. These compositions may also be incorporated into a fish net fiber during manufacture.

Marine coatings comprise a binder and solvent and optionally other ingredients. The solvent may be either organic solvent or water. The marine antifouling agents of the invention are suitable for use in both solvent and water based marine coatings. Solvent based marine coatings are preferred.

Any conventional binder may be utilized in the marine antifouling coating incorporating one or more of the antifouling agents of the invention. Suitable binders include, but are not limited to: polyvinyl chloride in a solvent based system; chlorinated rubber in a solvent based system; acrylic resins in solvent based or aqueous systems; vinyl chloride-vinyl acetate copolymer systems as aqueous dispersions or solvent based systems; butadiene-styrene rubbers; butadiene-acrylonitrile rubbers; butadiene-styrene-acrylonitrile rubbers; drying oils such as linseed oil; asphalt; epoxies; siloxanes; and the like.

The marine coatings of the present invention may optionally contain one or more of the following: inorganic pigments, organic pigments, or dyes, and controlled release materials such as rosin. Water based coatings may also optionally contain: coalescents, dispersants, surface active agents, rheology modifiers, or adhesion promoters. Solvent based coatings may also optionally contain extenders, plasticizers, or rheology modifiers.

A typical marine coating comprises 2 to 20% wt binders, 0 to 15% wt rosins/modified rosins, 0.5 to 5% wt plasticizers, 0.1 to 2% wt antisettling agent, 5 to 60% wt solvent/diluent, 0 to 70% wt cuprous oxide, 0 to 30% wt pigments (other than cuprous oxide), and 0 to 15% wt marine antifouling agent.

Coatings containing the marine antifouling agents of the invention may be applied to a structure to be protected by any of a number of conventional means. Suitable means of application include, but are not limited to, spraying; rolling; brushing; or dipping.

It is known in the art that the performance of marine antifouling agents may be enhanced by combination with one or more other marine antifouling agents. Thus, other known marine antifouling agents may be combined advantageously with the marine antifouling agents of this invention. The compounds of this invention may be combined with, e.g., tin based marine antifoulants. Such a combination has the advantage of reducing the amount of tin used and thereby lessening the amount of tin in the environment. Other marine antifouling agents useful in combination with the compounds of the invention include, but are not limited to: manganese ethylenebisdithiocarbamate; zinc dimethyl dithiocarbamate; 2-methyl-4-t-butylamino-6-cyclopropylamino-s-triazine; 2,4,5,6-tetrachloroisophthalonitrile; N,N-dimethyl dichlorophenyl urea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthio-sulfamide; zinc 2-pyridinethiol-1-oxide; tetramethylthiuram disulfide; copper-10% nickel alloy solid solution; 2,4,6-trichlorophenylmaleimide; 2,3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl (bispyridil) bismuth dichloride; 2-(4-thiazolyl)-benzimidazole; pyridine triphenyl borane; pyridine triphenyl borane; phenylamide compounds; pyridazinone compounds; or 2-haloalkoxyaryl-3-isothiazolones. Suitable 2-haloalkoxyaryl-3-isothiazolones include, but are not limited to: 2-(4-trifluoromethoxyphenyl)-3-isothiazolone, 2-(4-trifluoromethoxyphenyl)-5-chloro-3-isothiazolone, and 2-(4-trifluoromethoxyphenyl)-4,5-dichloro-3-isothiazolone.

The following examples are presented to illustrate further various aspects of the present invention, but are not intended to limit the scope of the invention in any aspect.

EXAMPLE 1

Tests were conducted to determine the toxicity of the marine antifouling agents of the invention to Amphora. Amphora are indicative of soft fouling organisms.

*Amphora coffeaeformis* var. perpusilla was isolated from a natural biofilm and cultured axenically in Guillard's F2 medium. A log phase culture of Amphora was diluted with the F2 medium to give a chlorophyll α concentration of 0.25 µg/mL. Chlorophyll α was measured by passing a measured volume (FV) of cell culture through a 3 µm pore, 25 mm diameter cellulose nitrate filter. The filter plus trapped algal cells was transferred to a glass tube. A measured volume (SV) of DMSO solvent was added to the glass tube. The tubes were incubated for 1.5 hours in darkness. After incubation, the absorbance of the sample was read in a spectrophotometer at 630 and 664 nm against a DMSO/filter blank. The chlorophyll a concentration can be calculated using the following equation:

Chlorophyllα(μg/mL)=11.47×Abs₆₆₄-0.4×Abs₆₃₀×SV/FV

Ten μL of the diluted culture was pipetted into glass tubes. Ten μL of marine antifouling agent or, in the case of controls, DMF was added to each glass tube. The tubes were incubated on an illuminated orbital shaker at 20° C. for 96 hours before the chlorophyll a concentration of each tube was measured. Three replicates of each treatment were used. The effects of marine antifouling agents are calculated as % inhibition of the mean control. The EC 50 is the dose effective at preventing 50% growth. The EC 100 is the dose effective at preventing 100% growth. Results of the tests are shown below.

TABLE 1

Activity Against *Amphora coffeaeformis* var. perpusilla (ppm)

| Compound | EC 50 | EC 100 |
|---|---|---|
| 36 | 1.9 | 5 |
| 138 | 2.5 | 20 |
| 146 | 3 | 20 |

Compounds showing activity against Amnphora in the low ppm range are considered active against soft fouling organisms. These results demonstrate the compounds of this invention are efficacious against soft fouling organisms in low concentrations.

EXAMPLE 2

Test were conducted to determine the toxicity of the marine antifouling agents of the invention to Artemia. Artemia are indicative of hard fouling organisms.

Substitute ocean water was prepared following ASTM Method D 1141-90. The water was sterilized by filtration through a 0.22 micron cellulose acetate membrane filter. San Francisco Bay Brand® Artemia salina cysts were purchased from a local aquarium supply store. The cysts were hatched in a 250 mL Erlenmeyer flask. The Artemia cysts (0.2 g) were weighed into a sterilized flask. One hundred mL of sterile ASTM sea water was added to the flask. The flask was placed on an orbital shaker set at approximately 150 rotations per minute and 28° C. After 24 hours, the contents of the flask were poured into a separatory funnel. The egg shells were separated from the Artemia nauplii (larvae), as the shells floated to the top. The nauplii were returned to the flask for another 24 hours shaking. The inoculum was prepared by pouring the nauplii into a crystallizing dish 48 hours after the cysts were originally placed on the shaker. After the nauplii congregated, they were taken up in a sterile serological pipette and transferred into another crystallizing dish. The suspension was stirred with a magnetic stirrer enough to keep the nauplii in suspension. Eighty mL of sterile sea water was added to the suspension. Using an eight channel microliter pipetter loaded with wide bore pipette tips, 100 μL of the suspension was transferred into a column of a 96 well, flat bottom, tissue culture plate. The number of nauplii in 3 to 4 wells was counted under a microscope. The number was averaged, and the inoculum was adjusted through further dilution, to 25 to 30 nauplii per 100 mL.

Stock solutions of the compounds to be tested were prepared on a weight to volume basis. Stock solutions were prepared at 40 times the highest concentration to be tested. Solvents were chosen based on the solubility of the compound to be tested. Solvents used were DMSO, acetone, or isopropanol. The solvents were tested to make sure that they had no effect on the test results.

Ninety six well, flat bottom, tissue culture plates were used for these tests. One hundred ninety μL of sterile ASTM sea water was added to column 1 of each plate. One hundred μL of sterile ASTM sea water was added to columns 2 through 12 of each plate. Ten μL of a stock solution of one compound to be tested was added to the first three wells of column 1. The next 2 wells were skipped, as they serve as untreated controls. Ten μL of a stock solution of a second compound to be tested was added to the last three wells of column 1. Serial dilutions were performed by mixing and transferring 100 μL from column 1 to column 2, then from column 2 to 3, and the process was continued until all 12 columns were diluted. One hundred μL from column 12 was discarded. One hundred μL of the stirring Artemia inoculum was added to each well of the plate. The test plate was covered with a plastic tissue culture plate lid and incubated for 24 hours at 25° C.

Plates were read under a low magnification microscope 24 and 48 hours after the nauplii were added to the plate. The highest dilution in which all of the nauplii are dead is the $LC_{100}$. Nauplii are considered alive if any movement is seen during the viewing period. Results of this test are shown below.

TABLE 2

Artemia LC 100 (ppm)

| Compound | 24 Hours |
|---|---|
| 18 | <8 |
| 36 | 1 |

Compounds showing activity against Artemia in the low ppm range are considered active against hard fouling organisms. These results demonstrate that the compounds of this invention are efficacious against hard fouling organisms.

What is claimed is:

1. A method of inhibiting the growth of marine organisms on a marine structure in sea water or brackish water, comprising applying onto or into the marine structure an effective amount of a marine antifouling agent of formula (I);

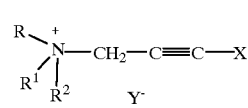

wherein:
R=$(C_1-C_{16})$ alkyl or $(C_1-C_5)$ alkyl substituted with $C(C=O)R^3$;
$R_1$ and $R_2$ are independently selected from $(C_1-C_3)$alkyl, or $R^1$ and $R^2$ are the same and are $(C_6-C_{12})$alkyl; or $R_1$ and $R_2$ together to form a 5- to 7-membered ring selected from the group consisting of pyrrolidinium, piperidinium, morpholinium, dimethylmorpholinium, hexamethyleneiminium, thiomorpholinium, and thiazolidinium, optionally substituted with one or more $(C_1-C_3)$ alkyl groups;
$R^3$ $(C_6-C_{12})$alkoxy;

X=halogen;

Y=an anion; and wherein the marine organisms whose growth is inhibited are selected from the group consisting of: soft corals, tunicates, hydroids, sponges, anemones, barnacles, tubeworms and molluscs.

2. A method according to claim 1 wherein X is bromine or iodine.

3. A method according to claim 2 wherein the marine antifouling agent is selected from the group consisting of: trioctyl-(3-bromopropargyl) ammonium benzenesulfonate, and 1-tetradecyl-1-(3-iodopropargyl)-pyrrolidinium 4-methylbenzenesulfonate.

4. A method according to claim 1 wherein Y is selected from the group consisting of halogen, phosphate, acetate, benzoate, citrate, tartrate, alkylsulfonate, arylsulfonate, and alkylsulfate.

5. A method according to claim 1 wherein the marine antifouling agent is incorporated in a carrier or a coating.

6. A method according to claim 5 wherein the amount of the marine antifouling agent in the carrier or coating is from 0.1 to 30% wt based on the weight of the structure to be protected or based on the weight of the coating to be applied.

7. A method according to claim 5 wherein the amount of the marine antifouling agent in the coating is from 0.5 to 15% wt based on the weight of the coating to be applied.

8. A method according to claim 5 wherein the amount of the marine antifouling agent in the carrier is from 0.5 to 20% wt based on the weight of the structure to be protected.

9. A method of inhibiting the growth of marine organisms on a marine structure in sea water or brackish water, comprising applying onto or into the marine structure a marine organism inhibiting amount of 1-tetradecyl-1-(3-iodopropargyl)-pyrrolidinium 4-methyl-benzenesulfonate, wherein the marine organisms whose growth is inhibited are selected from the group consisting of: soft corals, tunicates, hydroids, sponges, anemones, barnacles, tubeworms and molluscs.

* * * * *